US00H002096H

(19) United States

(12) Statutory Invention Registration (10) Reg. No.: US H2096 H

Erderly et al. (43) Published: Jan. 6, 2004

(54) THERMOPLASTIC ELASTOMER COPOLYMER FILMS

(75) Inventors: Thomas Craig Erderly, Baytown, TX (US); John Hugh MacKay, Chicago, IL (US); Russell Harrel Narramore, Brentwood, TN (US)

(73) Assignee: Exxon Chemical Patents, I, Wilmington, DE (US)

(21) Appl. No.: 08/469,835

(22) Filed: Jun. 6, 1995

Related U.S. Application Data

(60) Division of application No. 08/189,465, filed on Jan. 31, 1994, now abandoned, which is a continuation-in-part of application No. 08/013,518, filed on Feb. 3, 1993, now abandoned.

(51) Int. Cl.[7] ..... C08L 9/00; C08L 53/00; C08F 293/00

(52) U.S. Cl. ..... 525/98; 525/93; 525/314

(58) Field of Search ..... 525/98, 93, 314

(56) References Cited

U.S. PATENT DOCUMENTS

| | | | | |
|---|---|---|---|---|
| 3,299,174 A | | 1/1967 | Kuhre et al. | 525/98 |
| 3,424,649 A | | 1/1969 | Nyberg et al. | 428/517 |
| 3,562,356 A | | 2/1971 | Nyberg et al. | 525/93 |
| 3,678,134 A | | 7/1972 | Middlebrook | 525/98 |
| 4,171,411 A | | 10/1979 | Ehrenfreund | 521/98 |
| 4,173,612 A | | 11/1979 | Kelly | 264/176.1 |
| 4,476,180 A | | 10/1984 | Wnuk | 428/220 |
| 4,479,989 A | | 10/1984 | Mahal | 428/35 |
| 5,272,236 A | * | 12/1993 | Lai et al. | 526/348.5 |
| 5,278,272 A | * | 1/1994 | Lai et al. | 526/348.5 |

FOREIGN PATENT DOCUMENTS

EP 0 114 964 A1 8/1984

* cited by examiner

*Primary Examiner*—Michael J. Carone
*Assistant Examiner*—Aileen B. Felton
(74) *Attorney, Agent, or Firm*—Douglas H. Elliott; Moser, Patterson & Sheridan, L.L.P.

(57) ABSTRACT

Disclosed are (1) a thermoplastic elastomeric film comprised of an elastomeric arene-diene block copolymer and particular ethylene/β-olefin copolymers having low ethylene crystallinity and (2) the process of preparing films thereof. The disclosed films have superior strength and elasticity characteristics which render them particularly useful in apparel and healthcare items such as disposable diapers.

4 Claims, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

BASIC BLOWN FILM LINE

BASIC BLOWN FILM LINE

THERMOPLASTIC ELASTOMER COPOLYMER FILMS

This is a divisional of application Ser. No. 08/189,465 filed on Jan. 31, 1994 now abandoned which is a continuation in part of Ser. No. 08/013,518 filed Feb. 3, 1993 now abandoned.

FIELD OF INVENTION

This invention relates to thermoplastic elastomer blends of elastomeric block copolymers and certain olefin copolymers and, more specifically, to the fabricated films of the blends which exhibit high tensile strength and elasticity.

BACKGROUND OF THE INVENTION

Thermoplastic elastomers are readily commercially available and are fabricated as elastomeric films in products such as disposable diapers, leggins, waistbands and gloves. Typically, these elastomeric films have been made of elastomeric block copolymers, combinations of elastomeric block copolymers and liquid butadienes, combinations of elastomeric block copolymers and ethylene vinyl acetate copolymers, thermoplastic urethanes, ethylene-propylene rubbers (EP or EPR), including ethylene-propylene diene terpolymers (EPDM), natural rubbers and combinations of polyester copolymers and ethylene-vinyl acetate copolymers. Each of these materials has suitable properties for elastomeric films, such as low tensile set, low modulus, and high elongation, but each also has acknowledged deficiencies. For example, elastomeric films containing thermoplastic urethanes, copolyesters and/or ethylene vinyl acetate copolymers are expensive due to the cost of raw materials. The tensile set and modulus of films made of these well known elastomers are acceptable for many applications, but even greater advantages would be realized from films fabricated from elastomeric materials with lower tensile set and lower modulus.

It is well known to blend thermoplastic polymers in varying proportions with thermoplastic rubbers. Thermoplastic polymers such as polypropylene (meaning isotactic or crystalline polypropylene), polystyrene, polyethylene, ethylene-vinyl acetate copolymer, and polyurethane have been blended with thermoplastic rubber to effect compositions having varied thermoplastic and/or elastomeric properties.

The present invention relates to thermoplastic elastomer films made of elastomeric block copolymers and polyethylene/x-olefin copolymers. The relevant prior art to same includes the following:

A) U.S. Pat. No. 4,476,180 describes elastomeric films comprising from about 40% to about 80% of a thermoplastic block copolymer of styrene-butadiene-styrene (S-B-S) and from about 20 to about 60% of an ethylene/vinyl acetate copolymer (EVA), the fabricated films of which demonstrate good tensile strength and elasticity. While these films demonstrate suitable properties for most elastomeric film applications, the shortcomings of these films are (1) a significantly reduced elasticity of the patented blend as compared to the elastic property of the pure elastic S-B-S copolymer; (2) difficulty in processing of the blend; and (3) typically excessive blocking of the S-B-S elastomeric copolymer. U.S. Pat. No. 4,977,014 attempted reduction of these shortcomings by adding polystyrene to the '180 blend composition of the '180 patent.

B) Japanese patent application No. 554-120646 published on Sep. 19, 1979 discloses a composition of a styrene-butadiene elastomeric copolymer and ethylene/alphaolefin copolymer, the sole use of which composition was ineffective in film formation. This composition was rendered film-forming when a high styrenic styrenebutadiene copolymer was used as a third component. The ethylene/α-olefin copolymer has a density of 0.87 to 0.90, and is of low crystallinity.

While all of the cited elastomeric blend film art demonstrates certain advantages relating to processability, or physical characteristics such as softness, tensile strength or elasticity, they all fail to teach or appreciate the use of elastomeric block copolymer and linear low density polyethylene ("LLDPE") blends as demonstrated in the present invention. Consequently, the prior art elastomer/polyolefin blends retain certain deficiencies relating to film fabrication for apparel or healthcare use.

As any garments or healthcare products are worn, the elastic polymers used therein must have enough elastic strength to hold any of these items snugly in place. Conversely, an unworn garment or item must have a high degree of elastic recoverability so that the elastomeric polymer used therein returns essentially to an original shape during non-use. Additionally, any elastomeric films used in apparel items must also demonstrate a high degree of repeatability as any such items are worn over a long period of time. These conditions and constraints dictate the suitability of those elastomeric compositions of the prior art which can be fabricated into articles for garment or wear use.

As indicated above, typical elastic materials utilized for clothing or healthcare applications include the thermoplastic elastomeric films of U.S. Pat. No. 4,476,180 which contain elastomeric block copolymers of monoalkenyl arenes (styrene) and conjugated dienes (butadiene). These films generally exhibit good strength and elastic properties but also undesirable excessive blocking. Blocking is the tendency of a film to adhere to itself. When films made from block copolymers of monoalkenyl arenes and conjugated dienes are stored on a roll or in stacks, the film layers become difficult to unroll or unstack over a period of time due to their blocking tendency. Such blocking tendency can cause the film to tear when it is being unwound from a roll or being unstacked. To avoid such blocking it is generally necessary to add significant quantities of slip and anti-block agents to the film blend. The addition of these materials is undesirable because such material can accumulate on the film fabrication apparatus, particularly the rollers, and this accumulation can result in significant down time for machine cleaning.

It now has been found that the addition of certain LLDPE copolymers to elastomeric block copolymers of monoalkenyl arenes and conjugated dienes results in films having substantially reduced blocking tendency while exhibiting optimum elastic properties.

BRIEF SUMMARY OF THE INVENTION

The instant invention is a thermoplastic elastomeric film comprising (a) from about 20% to 70% of an elastomeric block copolymer having the general configuration:

A—B—A wherein the polymeric blocks A comprise monoalkenyl arene polymer end blocks and block B comprising an elastomeric conjugated diene polymer mid-block, the blocks A comprising from about 8 to 55% by weight of the block copolymer having a melt index of less than about 100; and (b) from about 20% to 70% of an LLDPE "plastomer" (as defined hereinafter) copolymer having less than 35% ethylene crystallinity. Particular LLDPE plastomer copolymers for use in the present blends include linear low density ethylene/a-olefin copolymers having densities from about 0.86 to 0.90 g/cm$^3$, molecular weight distributions of less than 6 and melt indices of between 0.2–1000 g/cm$^3$.

The LLDPE plastomer copolymers to be used in accordance with the present invention have very low ethylene crystallinity. The films made from blends of these low crystalline ethylene copolymers and elastomeric copolymers have the characteristics of high elasticity and low blocking tendency. These benefits occur because the instant film blends contain low crystalline plastomeric ethylene copolymers having certain characteristics of molecular weight distributions (Mw/Mn) -(MWD), melt index (MI), density, and crystallinity.

The films of the present invention have improved elastic recovery over those films of the prior art and provide benefits and applications where both low modulus and excellent elastic recovery are necessary as in the case of elastic components of disposable diapers. The instant films exhibit a low blocking tendency and consequently can be manufactured more efficiently and less expensively than other elastomeric films which require significantly more slip and antiblocking additives for their processed blends.

The elastomeric films of this invention are films of about 0.5 to 15 mils in thickness and may be produced by any well known film manufacturing processes such as these disclosed by J. H. Briston and L. L. Katan in *Plastic Films,* published by John Wiley & Sons, New York (2nd ed. 1983), herein incorporated by reference. Commonly known methods of producing film which may be utilized in the present invention include blowing, casting (extrusion and solvent), calendaring and extrusion methods, such as blow extrusion or slit die extrusion and cast embossed.

Briefly, the present invention is directed to a film comprising from about 20% to 70% of a monoalkenyl arene diene elastomeric block copolymer and from about 30 to 80% of a linear low density plastomeric polyethylene (LLDPE) copolymer having a density in the range of from 0.86 to 0.90, a melt index of from 0.2 dg/min to 1000 dg/min, an MWD in the range of less than 6, and a CDBI greater than about 45%.

A process for producing the elastomeric film of this invention comprises the steps of (a) providing a thermoplastic elastomeric film blend of (1) a block copolymer elastomer and (2) an LLDPE having a density of from about 0.86 to 0.900 g/cm$^3$, a MWD in the range of 2 to about 3.5, a melt index of less than 1000 dg/min, and an ethylene crystallinity of less than 35%; (b) extruding the blend composition through a die having a gap greater than about 5 mils and less than about 120 mils; (c) expanding the extruded film to a thickness of between 0.5 mils and about 15 mils by application of differential pressure as exerted by a gas and (d) rapidly cooling the expanded extruded film.

DETAILED DESCRIPTION OF THE INVENTION

Figure 1:
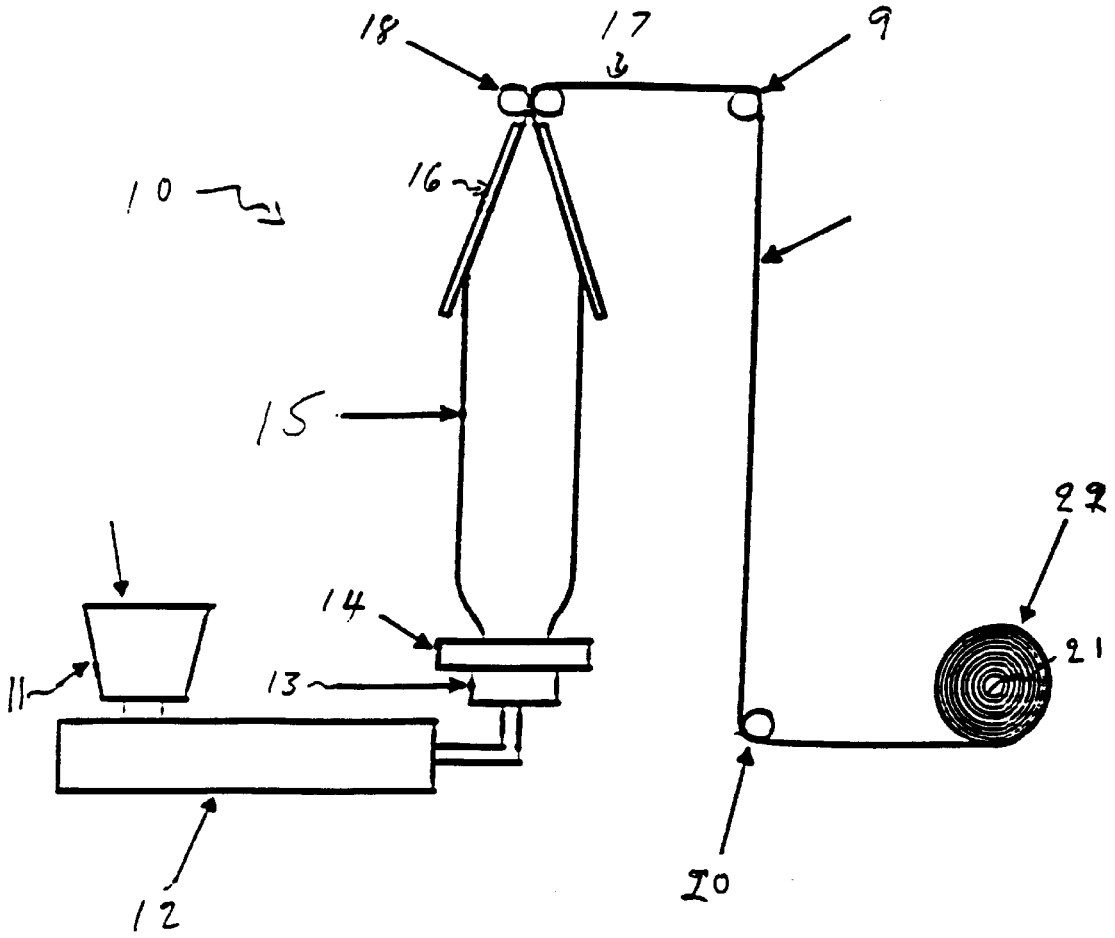
FIG. 1 is a schematic of the present invention showing the film of the present invention being made by a blown film apparatus and process, wherein the melted thermoplastic elastomer blend is blown into a tube and air cooled to form the film.

The thermoplastic elastomeric films of this invention comprise a blend of at least two copolymers. One copolymer is an elastomeric block copolymer containing blocks of a monoalkenyl arene copolymer and a conjugated diene polymer. The second component is selected from a group of highly amorphous thermoplastic ethylene copolymers having the primary characteristic of low crystallinity and low density. Optional ingredients which may also be included in the polymer blends of the present invention include small amounts of conventional anti-block concentrates and slip agents.

FIG. 1 shows a schematic of a blown film extrusion apparatus 10 and process for preparing the present film. The thermoplastic elastic pellets are fed into hopper 11 of extruder 12 where the elastic pellets are heated to above their melting point. The heated and extruded material is then fed through a ring shaped die 13 where it is formed into a sleeve or tube shaped film (not shown). The tube or sleeve so formed is subsequently blown and air cooled by an air ring 14 to form a bubble 15 of blown film. The bubble 15 is cooled further and then collapsed by converging frame elements 16 and then rolled into a flattened tube 17 by nip rollers 18. The flattened film 17 is then rolled on through idle rollers 19 and 20 by take up roll 21 to form film roll 22. A slitter (not shown) is an optional station that slits film 17 into two sheets if desired.

The instant thermoplastic elastomer film blends are formulated such that they can be processed on conventional thermoplastic film making equipment such as that of FIG. 1 or that used in a cast film processes. Thermoplastic elastomeric films produced with the instant blends are from about 0.5 mils to about 15 mils in thickness, preferably from about 1 to about 3 mils in thickness.

ELASTICITY

"Unload power" is the technical measure of elastic strength and an important elastic tensile property for elastomeric films to be used in garment or other skinwear applications. For example, in diaper applications, the unload power of an elastomeric article provides indication of the retractive force which holds the elastomeric article such as a backsheet against the infant's body. In all elastomeric materials, the unload power is lower than the load power (the force required to extend the film strip). This difference shows up as a hysterisis (the differential of the force to extend and the force to hold in place) and is larger for synthetic elastomers than in the case of a natural rubber.

"Residual set" refers to the change between the length of an elastomeric material before and after its extension to a certain length for a certain time for a certain number of cycles. For example, it would be measured by the percent change in length of a film after extension of the film to 150%, 200% and 300% of its initial length through 2.5 cycles. Each cycle would consist of extending the film beyond its initial length, holding the film extending for a time period, releasing the extending force, and allowing the film to return for a time period.

THE ELASTOMERIC BLOCK COPOLYMER

The elastomeric block copolymers contemplated for use herein are known materials having blocks of monoalkenyl arene polymer and blocks of conjugated diene polymer. The polymer blocks have the general configuration:

A—B—A and are arranged such that there are at least two monoalkenyl arene polymer end blocks A and at a least one elastomeric conjugated diene mid block B. The monoalkenyl arene copolymer blocks comprised from about 8% to about 55% by weight of the block copolymer. The molecular weight of the block copolymer is such that its melt index is less than about 100 as determined by ASTM Method D 1238 entitled "Standard Test Method for Flow Rates of Thermoplastics by Extrusion Plastomer" Condition E.

The term "monoalkenyl arene" includes those particular compounds of the benzene series such as styrene and its analogues and homologues including o-methyl styrene and p-methyl styrene, p-tert-butyl styrene, 1,3 dimethyl styrene p-methyl styrene in other ring alkylated styrenes, particularly ring methylated styrenes, and other monoalkenyl polycyclic aromatic compounds such as vinyl naphthalene, vinyl anthrycene and the like. For the present invention, the preferred monoalkenyl arenes are monovinyl, monocyclic arenes such as styrene and p-methyl styrene, styrene being particularly preferred.

It is critical to the present invention that the amount of monoalkenyl arene not exceed an amount of 55%, nor comprise an amount less than 8% by weight of the copolymer. Preferred amounts of monoalkenyl arene in the block copolymer are from 25% to 35%. Optionally, the monoalkenyl arene will be in an amount of about 30%. If a monoalkenyl arene is used in excess of 55 weight percent, the block copolymer is too stiff for the instant blends. The elastomeric block copolymers are "oil extended" which is the addition of a hydrocarbon oil and allows for improved processability and softer films. The oils are added to the commercial elastomeric copolymers in amounts of between 10% to 40%.

The block B comprises homopolymers of conjugated diene monomers, copolymers of two or more conjugated dienes, and copolymers of one or more of the dienes with a monoalkenyl arene as long as the blocks B are predominantly conjugated diene units. The conjugated dienes preferably used herein contain from 4 to 8 carbon atoms. Examples of such suitably conjugated diene monomers include: 1,3 butadiene (butadiene); 2-methyl-1,3 butadiene; isoprene; 2,3 dimethyl-1,3 butadiene; 1,3 pentadiene (piperylene); 1,3 hexadiene and the like.

For the instant films, the preferred monoalkenyl arene polymer is polystyrene; and the preferred conjugated diene polymers are polybutadiene and polyisoprene, especially preferred being polybutadiene. The preferred elastomeric block copolymers are commercially available as linear tri-block copolymers (A—B—A) from the Shell Chemical Company, Polymers Division, Houston, Texas, under the tradename KRATON and from Dexco Polymers of Houston, Texas, under the family trademark VECTOR. Especially preferred are the linear tri-block copolymers having polystyrene end blocks and a polybutadiene mid-block (S—B—S). Most commercially preferred are oil extended polymers such as KRATON D 2104 having a melt index of about 7 as determined by ASTM Method D 1238, Condition E and VECTOR 7400D, having a melt index of about 8.

The thermoplastic elastomeric films of the present invention may contain from about 20% to about 70% by weight of the plastomeric block copolymer; preferably from about 45% to about 65%; especially preferred being from about 50% to about 65%. The percentages herein are based on the total weight of the elastomeric film composition. As indicated, commercial grades of elastomeric block copolymers can be oil extended and the oil portion is not calculated as part of the percentage herein.

LINEAR LOW DENSITY PLASTOMER ALPHA-OLEFIN COPOLYMERS

As indicated above, the thermoplastic elastomeric film blends of the present invention are elastomeric block copolymers blended with amorphous linear low density ethylene/α-olefin copolymers. The LLDPE copolymers of the instant blends are termed "PLASTOMERS". The term "PLASTOMER" as used herein refers generally to a class of ethylene based polymers with a density with less than about 0.90 g/cm$^3$ down to about 0.86 g/cm$^3$ at a weighted average molecular weight (Mw), Mw, of greater than 20,000.

The melt index of the plastomers utilized in the invention are such that the plastomers can be extruded into a desired end product. In the preferred embodiment, the MI must be such that the plastomer will have sufficient drawability as desired. Generally the melt index is in the range of about 0.2 dg/min to about 1000 dg/min, preferably, the MI is at least about 0.5 dg/min, more preferably at least about 1 dg/min, preferably the maximum MI is about 20 dg/min, more preferably about 5 dg/min. In another embodiment, the MI is in the range of about 0.5 dg/min to about 50 dg/min, and more preferably in the range of about 1 dg/min to about 5 dg/min. MI as measured herein was determined according to ASTM D-1238 (190/2.16). These linear low density ethylene/a-olefin copolymers have an ethylene crystallinity between 5 to 35% and preferably between 5 to 15%. Densities were measured using ASTM D-1505 procedure, except that they were additionally conditioned by holding the resin for 48 hours at ambient temperature (23° C.) prior to density measurement.

The plastomer utilized in the elastomeric compositions of the present invention are selected from the group of polymers consisting of ethylene copolymerized with a $C_3$ to $C_{20}$ (α-olefins. The type of α-olefin comonomer selected for the plastomer herein will depend upon the type of film fabrication usage ultimately contemplated. Preferred x-olefins for use of comonomers in the plastomer polyethylene copolymers of the present film blends are $C_3$ to $C_8$ α-olefins, and the most preferred linear low density polyethylene copolymers are ethylene/propylene, ethylene/butene and ethylene/hexene copolymers.

Typically, these linear low density plastomers will generally comprise in the range of about 65 mole percent to about 93 mole percent ethylene, based on the total moles of monomer. Preferably the. amount of ethylene in these very low density copolymer plastomers ranges from about 68 to 91 mole percent. For complete effectiveness in the instant thermoplastic elastomeric film blends, the ethylene/a-olefin copolymer plastomers preferably have an ethylene crystallinity less than about 35% and, optimally, less than about 15%. Additionally, these plastomeric copolymers have a density in the range of about 0.860 g/cm$^3$ to about 0.90 g/cm$^3$ and preferably, an optimum density of about 0.860 g/cm$^3$ to 0.875 g/cm$^3$.

The melt index (MI) of these plastomers is such that the plastomer can be extruded or blown into the desired film product. In addition, the MI must be such that the plastomer will have sufficient drawability as desired. Generally the melt index is in the range of about 0.2 dg/min to about 20 dg/min, preferably between 1–10, and most desirably at about 2–6 dg/min.

The plastomers utilized in this invention have a molecular weight distribution such that the polymer will have the desired drawability and be processable into the desired film end product. The ratio of Mw/Mn (polydispersity) is generally in the range of about 2 to about 6, and most preferably in the range of about 2 to about 3.

A key characteristic of the LLDPE plastomer used in the elastomeric films of the present invention is their composition distribution. As is well known to those skilled in the art, the composition distribution of a copolymer relates to the uniformity of distribution of comonomer among the molecules of the copolymer. Metallocene catalysts are known to incorporate comonomer very evenly among the polymer molecules they produce. Thus, copolymers produced from a catalyst system having a single metallocene component have a very narrow composition distribution - most of the polymer molecules will have roughly the same. comonomer content and within each molecule the comonomer will be randomly distributed. With certain exceptions, Ziegler-Natta catalysts generally yield copolymers having a considerably broader composition distribution and, consequently, comonomer inclusion will vary widely among the polymer molecules.

In order to achieve the molecular weight distribution ratios outlined above, it is essential that the plastomer used in the instant elastomeric blend composition be prepared from catalysts that will achieve the narrow molecular weight distribution required herein. As already indicated, metallocene catalysts are highly flexible in that, by manipulation of catalyst composition and reaction conditions, they can achieve and control the molecular weight distribution of the copolymers to achieve an extremely narrow molecular weight distribution or polydispersity (Mw/Mn) of about 2, to a broad distribution (as in a polydispersity of about 8). Exemplary of the development of these metallocene catalysts for the copolymerization of the ethylene and (x-olefins of the instant plastomers are U.S. Pat. Nos. 4,937,299 to Ewen et al.; 4,808,561 to Welborn et al.; 4,814,310 to Chang et al. all the disclosures of which are hereby incorporated by reference. All of these publications describe polymerization processes using single site metallocene catalysts (SSC).

Another family of catalysts which can achieve equivalent results are those Ziegler type catalysts containing vanadium halides and oxyhalides (e.g., $VCl_4$, $VOCl_3$, $VBr_4$); and such compounds wherein at least one of valences of the metal is saturated by a heteroatom (in particular oxygen or nitrogen) bound to an organic group, such as vanadium tribenzoylacetonate, vanadyl diacetylacetonates and the haloacetylacetonates, vanadyl trialcoholates and haloalcoholates, the tetrahydrofuranates, etherates, the aminates of vanadium tri- and tetrachloride and of vanadyl trichloride, and the pyridinates and quinolinates of vanadium tri- and tetrachloride and of vanadyl trichloride. Vanadium compounds which are insoluble in hydrocarbons may also be used in preparing the catalysts, particularly, the organic salts such as e.g., vanadium triacetate, tribenzoate, and tristerate.

Specific methods for making the instant ethylene/a-olefin copolymer plastomers are taught in U.S. Pat. No. 4,871,705 to Hoel et al., hereby incorporated by reference. Utilizing single site metallocene catalysts of the cited prior art, the plastomer useful in the present elastomeric compositions can be produced in accordance with any suitable polymerization process, including a slurry polymerization, a gas phase polymerization, and a high pressure polymerization process.

CDBI is a measure of composition distribution. CDBI is defined as the weight percent of the copolymer molecules having a comonomer content. The CDBI of a copolymer is readily determined utilizing well known techniques for isolating individual fractions of a sample of the copolymer. One such technique is Temperature Rising Elution Fractimatin (TREF), as described in Wild, et al., *J. Poly. Sci. Poly. Phys. Ed.,* vol. 20, p. 441 (1982), which is incorporated herein by reference.

To determine CDBI, a solubility distribution curve is first generated for the copolymer. This may be accomplished using data acquired from TREF techniques described above. This solubility distribution curve is a plot of the weight fraction of the copolymer that is solubilized as a function of temperature. This is converted to a weight fraction versus composition distribution curve. For the purpose of simplifying the correlation of composition with elution temperature the weight fractions less than 15,000 are ignored. These low weight fractions generally represent a trivial portion of the plastomer of the present invention. The remainder of this description and the appended claims maintain this convention of ignoring weight fractions below 15,000 in the CDBI measurements.

From the weight fraction versus composition distribution curve the CDBI is determined by establishing what weight percent of the sample has comonomer content within 25% each side of the median comonomer content. Further details of determining CDBI of a copolymer are known to those skilled in the art, see, for example, PCT Patent Application WO 93/03093, published Feb. 18, 1993.

The composition distribution breadth index (CDBI) of the plastomers utilized in the present invention is generally about 45 percent or higher, preferably, the CDBI is about 50 percent or higher and more preferably, the CDBI is about 60 percent or higher, and most preferably, about 70 percent or higher.

The linear low density ethylene copolymers produced from the single site metallocene catalysts have been found to substantially reduce the blocking tendency of the instant elastomeric films containing them. Optimum blocking characteristics have been achieved with those elastomeric films comprising these plastomers and the styrene-butadiene-styrene copolymers sold as the VECTOR 7400 D series by Dexco Polymers. The advantage is the use of low slip concentrations, thereby reducing cost and improving final conversion efficiency by reducing slip plate-out during lamination and by reducing the quantity of adhesive required to laminate the film to another substrate. Additionally, elastic recoverability and substantially reduced tensile set were accomplished with all metallocene engendered plastomers and elastomeric copolymer blend films compositions of the present invention when compared to the compositions taught in the prior art.

As indicated above, the EVA/elastomeric copolymer blends of U.S. Pat. No. 4,476,180 represent state of the art thermoplastic elastomeric film blend materials and are widely accepted as the most satisfactory film fabrication compositions presently available. It has now been found that permanent set of the instant plastomer/elastomeric copolymer compositions represents as much as a 60% improvement over the recovery compatibility of those ethyl vinyl acetate/elastomeric copolymer compositions taught by U.S. Pat. No. 4,476,180.

The linear low density ethylene/(x-olefin copolymers referred to above have the characteristics of being low density and having low ethylene crystallinity giving them an amorphous crystalline structure and the physical characteristics of relatively high melt viscosity. This renders these copolymers generally miscible with the elastomeric block copolymers with which they are combined to form the film blends herein. While not to be construed as limiting, it is hypothesized that the ethylene/iolefin copolymers disclosed herein possess so little ethylene crystallinity that there is very little deformation set when these molecules are stretched and hence the resulting hysterisis benefits when used in conjunction with elastomeric block copolymers to form the highly elastic films of the invention.

The amounts of plastomer in the present elastomeric films range from 20 to 60% and preferably between 25 to 50% by weight of the total composition of the film. These ranges of the plastomer component of the instant blends insure the necessary processability and elastomeric properties of these plastomer/elastomeric block copolymer film blends.

OPTIONAL INGREDIENTS

Preferred thermoplastic elastomeric films of the present invention may contain from 0 to about 4% of commercial anti-block substances preferably from about 2% to about 3.5%. Preferred anti-block substances used in films of the present invention include the silicon based masterbatch sold as CM 19002 by Quantum Chemical Company.

Reduction in blocking in the films of the present invention can also be obtained by loading the film surface with small particles of powder such as talc, chalk, clay, silica, and similar materials. Powdered polymeric materials such as polytetrafluoroethylene can also be used to reduce blocking when applied to the surface of films of the present invention. Such film treatment can be used to reduce blocking alone or in combination with other anti-block methods described herein or otherwise known in the prior art. The quantity of powder anti-block substance commonly added to the surface of a film when used is from about 0.5 $g/m^2$ to about 5 $g/m^2$.

Anti-static agents may be incorporated in films of the present invention; examples of such agents included ethoxylated amines and quarternary amine salts having organic constituents of about 12 to 18 carbon atoms in length. Agents of this type slowly diffuse to the surface of the film and, because of their ionic character, form an electrically conductive layer on the surface of the layer of the film. Anti-static agents commonly constitute from about 1% to 5% of the weight of the films, when used.

While anti-blocking is a central characteristic of the present film blend, small amounts of slip agents will be incorporated into the films of the present invention to further reduce drag over rollers and other forming equipment. Examples of such agents are those commonly derived from amide fatty acids having from about 12 to 22 carbon atoms. Such agents may augment the superior anti-blockingvproperties of the films of the present invention. Such slip agents are commonly incorporated in films from about 0.05% to about 3% of the weight of the films when used. Again, the present film biends are superior in anti-blocking characteristics thereby reducing the need for such slip agents, the reduction of block tendency rendering film production more efficient and less expensive.

In order to minimize degradation of films of the present invention during processing by extrusion or other techniques heat stabilizers and antioxidants may be added to the polymer formulations. Examples of heat stabilizers that may be used are organic phosphite compounds and other organic substances such as trihydroxy butyrophenone. When used, heat stabilizers and antioxidants are incorporated into the polymeric formulations at levels of about 0.1% to about 2.5% by weight.

Degradation of the films of the present invention by exposure to ultraviolet light can be moderated by the addition of photostabilizers. An example such photostabilizers are well known in the prior art and included derivatives of benzophenone. Such photostabilizers are generally incorporated in the polymer formulations at a level from about 0.1% to about 3% when used.

Pigments may also be added to the polymer formulations to impart a particular color to the resulting films. Pigments are typically added to the resin blend in the form of concentrates, formulated to improved dispersion of the pigment at levels of from about 0.5% to about 4% when used.

The optional constituents described here and above may be used alone or in combination with any or all of the other optional constituents in the present film blends.

Film Fabrication

The invention provides a fabrication method for increasing the unload power and residual set of an elastic material. According to ASTM definitions relating to rubbers, elastic materials are considered those materials which rapidly return to approximately their initial dimensions and shape after substantial deformation by a weak stress and release of the stress. In the preferred embodiment, the elastic materials of the invention are considered to be those which, when stretch to one and half to twice their original length (1.5–2X) at room temperature (18° C. to 29° C.), and held at 1.5–2X for one minute, will retract to less than 1.0X within one minute after the deforming force is released.

The present invention is directed toward an elastic film having improved unload power and residual set produced by blown, cast or embossed extrusion processes. The film is formed by any suitable method well known in the art, or once formed, the film can be subjected to a combination of post orienting and/or annealing to effect changes in its unload power. Such methods of making film are discussed by the earlier cited J. H. Briston and L. L. Katan in *Plastic Films,* (2nd ed. 1983) and U.S. Pat. Nos. 4,436,520 and 5,066,526, the disclosures of which are herein incorporated by reference. Commonly know methods of producing film include casting (extrusion and solvent), calendaring and extrusion methods, such as blow, slit extrusion or cast die extrusion, or cast embossed extrusion. A preferred preparation of the instant composition is the blown film process of FIG. 1.

The invention in another embodiment is suitable for improving the unload power of thin elastic articles. Such thin elastic articles are commonly known as ribbon, tape, film, strip, sheet, and the like. The differences between these particular terms is generally dimensional. For example, tape is generally thought of as being narrower than film. For the purposes of this patent specification, the terms "ribbon", "tape", "film", "sheet", and "strip" are generally interchangeable.

Regardless of the method of first producing the film, once made, the film can be used as is, or it can be further processed to improve unload power of the film. This further processing is accomplished by a combination of orienting and/or annealing the film. In one embodiment, the annealing is conducted at a temperature between the film softening point and melting point. Orientation of non-elastic films such as polypropylene, polystyrene, nylon and polyethylene terphthalate to improve clarity, impact strength and particularly in the case of polypropylene, its barrier properties, is well known in the art. The orienting and annealing of the film may be carried out monoaxially in the machine direction (MD) or the traverse direction (TD) or in both directions (biaxially) either simultaneously or sequentially using conventional equipment and processes following cooling of the film.

Blown films are preferably stretched in machine direction or in both directions. Cast films are preferably stretched in the machine direction. Generally, for orientation in the machine direction, the film is passed around two rollers driven at different surface speeds and finally to take up roller. The second driven roller which is closest to the take up roll is driven faster than the first driven roller. As a consequence, the film is stretched between the driven rollers. Conventional "godet" stands as are well known in the art may also be utilized.

Film orientation in another embodiment may also be carried out in a tentering device with or without machine direction orientation to impart transverse direction orientation in the film. The film is gripped by the edges for processing through the tentering device. For most final applications, the film is monoaxially oriented in the machine dirtection.

The morphology of the instant elastomer/plastomer films can be viewed as a matrix of amorphous material interspersed with crystallites. For orienting, it is generally necessary that the film be heated to between its softening point and its melting point. This heating is necessary to allow extension or orientation o be induced into the film. Since the temperature is etween the film softening point and melting point, the smaller imperfect crystallites will melt, whereas larger more perfect crystallites of the plastomer will remain. The molecules in the amorphous matrix become oriented or extended depending on the draw ratio and other material and fabrication parameters.

In one embodiment, the film of the invention is annealed at a temperature between the film softening point and melting point. The annealing step is necessary to anneal or perfect the crystallites that survived the orienting step and to relax out stresses. This annealing aids in maintaining the orientation or extension induced in the orienting step. The annealing temperature is preferably less than the orienting temperature. Generally once the film leaves the annealing step, ambient cooling is sufficient. In most cases, the film from the annealing step is then spooled in a winding unit.

Industrial Applicability

The thermoplastic elastomeric films of the present invention may be used in a wide variety of applications where thin, elastic material would be useful. Such films are particularly useful as low cost elastic members for disposable wearing apparel such as diapers, training pants, feminine hygiene devices, medical gowns, gathered laminate garments, non-woven head bands, sports apparel, bandages and protective clothing.

EXAMPLES

The following examples illustrate preferred embodiments of the invention in comparison to similar standard compositions not employing the plastomeric olefin copolymers illustrated in the thermoplastic elastomeric film blends of the present invention. All experiments were conducted with the materials indicated in the tables. All examples employed a styrenebutadiene elastomeric block copolymer in the commercial form of Shell's KRATON D 2104 and Dexco's VECTOR 7400D which was blended with the olefin copolymers of the present invention.

A. COMPOSITION

The character and commercial source of the elastomeric and LLDPE copolymer resins used in the examples are listed in the following table.

TABLE I

| RESIN | RESIN TYPE | MI (DG/MIN) | DENSITY (G/CM$^3$) | COMONOMER | SUPPLIER |
|---|---|---|---|---|---|
| KRATON D-2104 | SBC | 4.25 | .930 | SBS | SHELL |
| VECTOR 7400D | SBC | 8.0 | .930 | SBS | DEXCO |
| LD-767 | EVA | 3.2 | — | 28% VA | EXXON |
| XS-12.04 | EMA | 3.0 | — | 28% MA | EXXON |
| TAFMER P0480 | MITSUI | 1.0 | .867 | EP | MITSUI |
| TAFMER P0480 | MITSUI | 3.0 | .867 | EP | MITSUI |
| TAFMER P0480 | MITSUI | 8.0 | .867 | EP | MITSUI |
| EXACT WS-9905 | EXXPOL | 4.1 | .874 | EB | EXXON |
| EXACT 4049 | EXXPOL | 4.5 | .873 | EB | EXXON |
| MBX-6 | MB | 8.6 | 1.176 | SLIP = 3%<br>A/B = 35%<br>A/O = 0.2%<br>CARRIER = LDPE | EXXON |

The compositions employed in the following examples contain an additive package of 0.2% of IRGANOX 1076 stabilizer sold by Ciba-Geigy Corporation, 0.3% of Eucaramide Slip Crodamide ER sold by Humko Chemical and 3.5% of Superfloss Silica anti-blocking agent sold by Manville Corporation. The anti-block was introduced in the form of a 50/50 (LDPE/anti-block) masterbatch (CM 19002) supplied by Quantum Chemical Company, for hot melt blend formulations. The melt index of the film compositions or components was determined according to ASTM Method D 1238, condition E as indicated.

B. COMPOUNDING

All formulations identified in Table III, Examples 6–11, were hot melt compounded on a 57 mm twin screw ZSK Extruder manufactured by Werner Pfleiderer at melt temperatures not exceeding 350° F. The extruder has a length diameter ratio (L/D) of 24:1. Feed rates ranged from 500 to 300 lbs/hr and water temperatures ranged from 78 to 55° F. The blends of Table II were dry blended as indicated.

C. FILM FABRICATION

Film was produced on a 1½ inch Egan Blown Film extruder having 24:1 L/D and a 3 inch die. The melt temperature of the film blend was about 320° F. The BUR was 2:1 and films of about 2 mil thickness resulted.

The blowup ratio of blown films is calculated as the ratio of the total lay-flat with blown film to the circumference of the inner circle of the film dye.

The blown film conditions in t he Egan Line extrusion process for the two sets of samples subjected to the respective 200% and 150% extensions are outlined in Tables II and III as follows.

Two examples of films fabricated for data of Table VI were prepared on a 4½ inch commercial film line at Exxon Chemical Company in Lake Zurich, Ill.

TABLE II

BLOWN FILM EXTRUSION CONDITIONS FOR SAMPLES SUBJECTED TO 200% EXTENSION

| SAMPLE ID | BUR | DIE GAP (MIL) | YAG (MIL) | EXT SPEED (RPM) | EXT. LOAD (AMPS) | EXT. PRESS (PSI) | FLH (IN) | MELT TEMP (° F.) | SCREEN PACK |
|---|---|---|---|---|---|---|---|---|---|
| 001 (CONTROL) | | | | | | | | | |
| KRATON D2104, SBC 28% EVA | 2.1 | 35 | 2.05 | 30 | 20 | 1450 | 9.5 | 320 | 40/120/40 |
| 002 | | | | | | | | | |
| KRATON D2104, SBC 28% EMA | 2.1 | 35 | 2.37 | 30 | 22 | 1150 | 9.5 | 358 | 40/120/40 |
| 003 | | | | | | | | | |
| KRATON D2104, SBC 28% TAFMER P0480 | 2.1 | 35 | 2.40 | 30 | 28 | 2100 | 10 | 410 | 40/120/40 |
| 004 | | | | | | | | | |
| KRATON D2104, SBC 28% TAFMER P0280 | 2.1 | 35 | 2.32 | 30 | 25.5 | 1600 | 10 | 410 | 40/120/40 |
| 005 | | | | | | | | | |
| KRATON D2104, SBC 28% TAFMER P0180 | 2.1 | 35 | 2.19 | 30 | 26 | 1650 | 9.5 | 378 | 40/120/40 |

NOTE:
ALL BLEND FORMULATIONS ARE DRY BLENDED WITH A SLIP, ANTIBLOCK MASTERBATCH (MBX-6).
FILM FABRICATED ON A 1½", 24:1 L/D FILM EXTRUDER.

TABLE III

BLOWN FILM EXTRUSION CONDITIONS FOR SAMPLES SUBJECTED TO 150% EXTENSION

| SAMPLE ID | BUR | DIE GAP (MIL) | YAG (MIL) | EXT SPEED (RPM) | EXT. LOAD (AMPS) | EXT. PRESS (PSI) | FLH (IN) | MELT TEMP (° F.) | SCREEN PACK |
|---|---|---|---|---|---|---|---|---|---|
| 006 (CONTROL) | | | | | | | | | |
| KRATON D2104, SBC 28% EVA | 2.1 | 35 | 2.19 | 30 | 23 | 1770 | 9 | 320 | 20/40/80/20 |
| 007 (CONTROL) | | | | | | | | | |
| KRATON D2104, SBC 28% EVA | 2.1 | 50 | 2.89 | 30 | 22 | 1090 | 9.5 | 325 | 20/40/20 |
| 008 | | | | | | | | | |
| KRATON D2104, SBC 28% EXXPOL | 2.1 | 35 | 2.31 | 30 | 29 | 2460 | 10 | 320 | 20/40/80/20 |
| 009 | | | | | | | | | |
| KRATON D2104, SBC 46% EXXPOL | 2.1 | 35 | 2.25 | 30 | 32 | 2660 | 10 | 320 | 20/40/80/20 |
| 0010 | | | | | | | | | |
| VECTOR 7400D, SBC 28% EXXPOL | 2.2 | 50 | 2.68 | 30 | 29 | 1630 | 12.5 | 327 | 20/40/20 |
| 0011 | | | | | | | | | |
| VECTOR 7400D, SBC 46% EXXPOL | 2.2 | 50 | 2.63 | 30 | 29 | 1580 | 12.5 | 327 | 20/40/20 |

NOTE:
ALL BLEND FORMULATIONS HOT MELT COMPOUNDED ON A TWIN SCREW EXTRUDER WITH SLIP, ANTIBLOCK MASTERBATCH.
FILM FABRICATED ON A 1½", 24:1 L/D FILM EXTRUDER.

D. HYSTERESIS

The ultimate tensile strength and elongation were determined according to ASTM D-882-81 Method using an INSTRON Model 1122 Tester. The tensile properties of the film were measured in the direction of extrusion of the film (machine direction, MD); and in the direction perpendicular to the direction of the extrusion (crossmachine direction, CD or traverse direction (TD)). Test specimens were cut along the direction of extrusion of the film (MD) and along the traverse direction in segments of 1 inch wide and 6 inches long.

The hysteresis testing is an Exxon variation of a procedure described by DuPont in its brochure on its polyether urethane elastic product, T-722A. In the Exxon variation, 1 inch×6 inch strips are subjected to a strain rate of 150% or 200% or 300% with a jaw gap separation of 2" and crosshead speed of 20"/min. the hysteresis stress/strain curve is plotted on a chart also traveling a 20"/min. Both the extension and retraction crosshead speeds (20"/min.) were the same and performed on an Instron model 1123. The film was held for 60 seconds at maximum extension and then retracted and held for 30 seconds relaxation prior to the next cycle. This was repeated 2½ times. Key pieces of information that are extracted from these stress/strain plots are the maximum force (modulus) of each cycle, the residual set or permanent set (the degree of deformation as measured by the point of stress divided by total strain/cycle), and the unload force or contractive power as measured from the last retraction cycle at various elongations. Generally, five specimens were tested for each sample, with mean values over these samples developed.

For the films of the present invention, the preferred hysteresis properties which are obtained are as follows:

Permanent set (%) (obtained through use of a modification of ASTM D-1682 wherein the stretching is cycled rather than continued through film failure) (150% extension, one cycle, MD): preferably less than 40, more preferably in the range of about 5 to about 25, most preferably less than 10–20; and/or Permanent set (%) (150% extension, 1 cycle, TD): preferably less than 40%, more preferably in the range of about 5 to about 25, most preferably less than 10–20% and/or;

Permanent set (%) (200% extension, 1 cycle, MD): preferably less than 45%, more preferably in the range of about 5 to about 25%, most preferably 5–15%; and/or Permanent set (%) (200% extension, one cycle, TD): preferably less than 45%, more preferably in the range of about 5 to about 25%, most preferably in the range of about 5–15%; and/or Permanent set (%) (300% extension, 1 cycle, MD): preferably less than 50%, more preferably in the range of about 20 to about 40%, most preferably 15–30%; and/or Permanent set (%) (300% extension, one cycle, TD): preferably less than 50%, more preferably in the range of about 20 to about 40%, most preferably in the range of about 15–30%; and/or Table 4 lists comparative data for the following Examples 1–5 with Example 1 being the control using the standard blend formulations. These examples were dry blended, then extruded on a 1 ½" Egan blown film lab line. Melt strength, film appearance, and openability, were measured on line. Hysterisis testing was preferred at 200% extension in order to compare improvements to elastic recoverability.

EXAMPLE 1

Blend Formulation:

| Component | Percentage |
|---|---|
| KRATON D2104 | 63% |
| LD 767.36 | 27% |
| MBX - 6 | 10% |

The material extruded satisfactorily with good melt strength as indicated by the observed bubble stability. The collapsed film was peeled with no sticking or fusing, thereby qualitatively determining "openability" as good and given an "A" rating (based on an A, B, C, D scale with "A" being good and "D" being poor). The film appearance rating (FAR) was slightly grainy and qualitatively given a "B" rating based a scale which qualifies a totally clear film as an "A" rating while an opaque film would be rendered a "D". This film is the "control" and will be used as the comparison hereinafter.

EXAMPLE 2

| Blend Component | Percentage |
|---|---|
| KRATON D2104 | 63% |
| XS 12.04 | 27% |
| Ethyl Methyl Acrylate ("EMA") | |
| MBX - 6 | 10% |

The film produced had a less grainy appearance and rated a FAR of "B". Openability was slightly less than Example 1 and rated a "B" to "C". Elastic recoverability was slightly improved over the control. The MD tensile set was 20% vs 22.6% (13% improvement) while the TD had a 17% improvement (18% vs. 21.2%).

EXAMPLE 3

| Component | Percentage |
|---|---|
| KRATON D2104 | 63% |
| TAFMER P0480 | 27% |
| MBX - 6 | 10 |

The material processed well with observed excellent bubble stability and received a FAR rating of "A". The openability was slightly less ("B") than the control but tensile set was substantially improved. The MD set was 14.1% vs. 22.6% (60% improvement) while the TD set displayed a 35% improvement (15.7% vs. 21.2%).

EXAMPLE 4

| Component | Percentage |
|---|---|
| KRATON D2104 | 63% |
| TAFMER P0280 | 27% |
| MBX - 6 | 10% |

Good extrusion performance with an excellent FAR rating of "A" and comparable openability to the control thereby deserving of an "A" rating. Again the tensile set properties were substantially improved over the control. The MD permanent set had an improvement of 50% (15.1% vs. 22.6%) while the TD had an improvement of 39% (15.3% vs. 21.2%).

EXAMPLE 5

| Component | Percentage |
|---|---|
| KRATON D2104 | 63% |
| TAFMER P0180 | 27% |
| MBX - 6 | 10% |

The material was very splitting and broke upon extension in the TD. The FAR rated a "IC" and openability rated a "B". The tensile set could not be measured in the TD but the MD had a 53% improvement over the control (14.8% vs. 22.6%).

The results of the first five examples are outlined in Table IV. Example 2 utilized EMA as a polyolefin component of the elastomeric blend to illustrate the use of another known component commonly cited, but not commercially preferable, for use in elastomeric blends. The overall conclusions reached for those specific embodiments of the invention in Examples 3–5 are that substantial improvements to tensile set (elastic recoverability) can be achieved by replacing the EVA component of the standard commercial blend as taught in prior art U.S. Pat. No. 4,476,180, with a LLDPE plastomer copolymer such as the TAFMER P0480 and P0280 copolymers of Mitsui Corporation of Japan. As much as a 60% improvement has been demonstrated for tensile set (recoverability) over the control while maintaining comparable modulus and extrusion process performance in the preparation of the films as illustrated in the data of Table IV. Note that the recoverability of the film of Example 2 utilizing EMA demonstrated a tensile set which improved slightly over the EVA control, but was not as impressive as Examples 3–5 utilizing the LLDPE's of the present invention.

were hot melt compounded on a 57 mm Zsk twin screw extruder described previously. Compounds were then run on a 1½" Egan blown film line using both a 35 and 50 mil die gap. Film appearance, openability and bubble stability were measured qualitatively on line. Hysteresis testinzg was performed at 150% extension per the previously described method herein in order to compare improvements to elastic recoverability and any improvements to the process.

Comparisons were made with comparable die gaps. Therefore, Example 8 demonstrates a 22% improvement to tensile set over the control in Example 6 using the same amount of LLDPE (28%). Example 9 demonstrates comparable modulus and tensile set to the control of Example 6 using elevated amounts of LLDPE (48%). Similar results are obtained when comparing Example 7 with Examples 10 and 11.

TABLE IV

| | | | | | HYSTERESIS RESULTS @ 200% EXTENSION | | | | | | |
|---|---|---|---|---|---|---|---|---|---|---|---|
| | | | | | MODULUS | | % TENSILE SET | | | | |
| | | | DIE GAP | YAG | (1) | (2) | (1) | (2) | UNLOAD FORCE (G) | | |
| SAMPLE ID | | BUR | (MIL) | (MIL) | (G) | (G) | (%) | (%) | 25% | 50% | 200% |
| 001 (CONTROL) | | | | | | | | | | | |
| KRATON D2104, SBC | MD | 2.1 | 35 | 2.05 | 313 | 270 | 18.7 | 22.6 | — | 21.2 | 227 |
| 28% EVA | TD | | | | 216 | 193 | 17.4 | 21.2 | — | 17.9 | 164 |
| 002 (CONTROL) | | | | | | | | | | | |
| KRATON D2104, SBC | MD | 2.1 | 35 | 2.37 | 361 | 311 | 17.7 | 20.0 | — | 29.7 | 262 |
| 28% EMA | TD | | | | 215 | 196 | 15.3 | 18.1 | — | 17.7 | 162 |
| 003 | | | | | | | | | | | |
| KRATON D2104, SBC | MD | 2.1 | 35 | 2.40 | 308 | 257 | 12.1 | 14.1 | 12.1 | 49.3 | 228 |
| 28% TAFMER P0480 | TD | | | | 215 | 193 | 13.8 | 15.7 | — | 33.3 | 169 |
| 004 | | | | | | | | | | | |
| KRATON D2104, SBC | MD | 2.1 | 35 | 2.32 | 256 | 214 | 13.1 | 15.1 | 5.1 | 36.7 | 189 |
| 28% TAFMER P0280 | TD | | | | 166 | 145 | 12.5 | 15.3 | 2.3 | 26.8 | 122 |
| 005 | | | | | | | | | | | |
| KRATON D2104, SBC | MD | 2.1 | 35 | 2.19 | 203 | 164 | 12.5 | 14.8 | 6.7 | 28.7 | 147 |
| 28% TAFMER P0480 | TD | | | | Broke | Broke | Broke | Broke | Broke | Broke | Broke |

The following Table V lists comparative hysteresis data for Examples 6 through 11 at 150% extension. All samples

TABLE V

| | | | | | HYSTERESIS RESULTS @ 150% EXTENSION | | | | | | | |
|---|---|---|---|---|---|---|---|---|---|---|---|---|
| | | | | | MODULUS | | % TENSILE SET | | | | | |
| | | | DIE GAP | YAG | (1) | (2) | (1) | (2) | UNLOAD FORCE (g) | | MI | DENSITY |
| SAMPLE ID | | BUR | (MIL) | (MIL) | (G) | (G) | (%) | (%) | 25% | 50% | (DG/MIN) | (g/cm$^3$) |
| 006 (CONTROL) | | | | | | | | | | | | |
| KRATON D2104, SBC | MD | 2.1 | 35 | 2.19 | 304 | 262 | — | 11.1 | — | — | 4.4 | .949 |
| 28% EVA | TD | | | | 286 | 265 | — | 10.3 | — | — | | |
| 007 (CONTROL) | | | | | | | | | | | | |
| KRATON D2104, SBC | MD | 2.1 | 50 | 2.89 | 554 | 479 | 11.2 | 13.2 | 37 | 109 | 4.1 | .941 |
| 28% EVA | TD | | | | 289 | 265 | 12.5 | 14.4 | 21 | 67 | | |

TABLE V-continued

| | | | | | HYSTERESIS RESULTS @ 150% EXTENSION | | | | | | | |
|---|---|---|---|---|---|---|---|---|---|---|---|---|
| | | | | | MODULUS | | % TENSILE SET | | | | | |
| | | | DIE GAP | YAG | (1) | (2) | (1) | (2) | UNLOAD FORCE (g) | | MI | DENSITY |
| SAMPLE ID | | BUR | (MIL) | (MIL) | (G) | (G) | (%) | (%) | 25% | 50% | (DG/MIN) | (g/cm$^3$) |
| 008 | | | | | | | | | | | | |
| KRATON D2104, SBC | MD | 2.1 | 35 | 2.31 | 292 | 267 | — | 9.13 | — | — | — | — |
| 28% EXXPOL | TD | | | | 362 | 330 | — | 8.57 | — | — | | |
| 009 | | | | | | | | | | | | |
| KRATON D2104, SBC | MD | 2.1 | 35 | 2.25 | 309 | 278 | — | 12.9 | — | — | 3.1 | .926 |
| 48% EXXPOL | TD | | | | 342 | 317 | — | 12.6 | — | — | | |
| 0010 | | | | | | | | | | | | |
| VECTOR 7400D, SBC | MD | 2.2 | 50 | 2.68 | 480 | 412 | 8.5 | 10.5 | 74 | 145 | 2.8 | .920 |
| 28% EXXPOL | TD | | | | 244 | 224 | 11.1 | 13.1 | 39 | 82 | | |
| 0011 | | | | | | | | | | | | |
| VECTOR 7400D, SBC | MD | 2.2 | 50 | 2.63 | 451 | 398 | 11.1 | 13.1 | 36 | 109 | 2.7 | .916 |
| 48% EXXPOL | TD | | | | 368 | 330 | 12.5 | 14.4 | 18 | 85 | | |

EXAMPLES 6 & 7 (Controls)

| Component | Percentage |
|---|---|
| KRATON D2104 | 63.7% |
| LD 767.36 | 28.8% |
| Spectrathene (CM 19002) | 7.0% |
| Euracamide | .3% |
| IR 1076 | .2% |

The Example 6 fabrication of the controls for the 150% hysteresis testing in Table V was performed using a 35 mil die gap while Example 7 used a 50 mil gap. Both had good bubble stability and FAR "A". The film appearance was improved over dry blends of Example 1 in that they displayed no grainy appearance. Openability was good but did display some blocking ("B" rating). Permanent set was somewhat better using the 35 mil die gap for Example 6 vs. 50 mil gap for Example 7. Also the MD modulus was higher for Example 7 vs. 6, but TD modulus was comparable.

EXAMPLE 8

| Component | Percentage |
|---|---|
| KRATON D2104 | 63.7% |
| EXXPOL WS-9905 | 28.8% |
| Spectrathene (CM 19002) | 7.0% |
| Euracamide | .3% |
| IR 1076 | .2% |

Film appearance (FAR "A") and bubble stability were excellent. Film openability was substantially superior to the control and given an "A+" but the motor load and pressure were higher. MD tensile set was 22% improved (9.13% vs. 11.1%) over the control Example 6 (Control). An unexpected finding was the improvement to openability using the EXXPOL polymer as a replacement to the commercially accepted EVA. This use of the EXXPOL LLDPE in place of the standard EVA will not only improve the processability, but will allow reduced slip levels, thus saving additive costs and downtime for downstream converters due to slip build up.

EXAMPLE 9

| Component | Percentage |
|---|---|
| KRATON D2104 | 46.25% |
| EXXPOL WS-9905 | 46.25% |
| Spectrathene (CM 19002) | 7.0% |
| Euracamide | .3% |
| IR 1076 | .2% |

Again bubble stability and FAR were excellent ("A" FAR rating) and openability was significantly improved over the controls and earned an "A++". Tensile set and modulus were comparable to the control of Example 6 at 35 mil die gap. The advantage over the Example 6 control is the reduced amount of slip agent and SBC component, thus reducing cost of fabricating the film.

EXAMPLE 10

| Component | Percentage |
|---|---|
| VECTOR 7400D | 63.7% |
| EXXPOL W5-9905 | 28.8% |
| Spectrathene (CM 19002) | 7.0% |
| Euracamide | .3% |
| IR 1076 | .2% |

This compound was compared against the Example 7 Control using the 50 mil die gap. Bubble stability and FAR were excellent ("A"). Film openability was significantly better than all other blends when the EXXPOL SSC and VECTOR SBC from the Dexco Company were compounded together and rated an A+++. Also the modulus and tensile set of this particular blend were substantially improved over the control (16% and 26% respectively) while the. unload force (contractive power) was comparable to the commercially satisfactory controls. The unexpected finding was the improved openability for the VECTOR SBC EXXPOL's blend compared with the controls employing the same additive package.

EXAMPLE 11

| Component | Percentage |
|---|---|
| VECTOR 7400D | 46.25% |
| EXXPOL WS-9905 | 46.25% |
| Spectrathene (CM 19002) | 7.0% |
| Euracamide | .3% |
| IR 1076 | .2% |

Film processability was comparable to the control (Example 7) but had somewhat higher load and pressure. The openability was comparable to Example 10 and substantially better than the EVA/KRATON blends. Modulus and tensile set were also comparable to the control showing that comparable properties can be achieved versus the control but at reduced SBC and slip additive levels which will substantially reduce costs and save downtime for convertors using embodiments of this invention.

EXAMPLE 12

| COMPONENT | PERCENTAGE |
|---|---|
| VECTOR 7400D | 60% |
| LD 767.36 | 32.1% |
| CM 19002 | 7% |
| EURACAMIDE | .7% |
| IR 1076 | .2% |

EXAMPLE 13

| COMPONENT | PERCENTAGE |
|---|---|
| VECTOR 7400D | 60% |
| EXACT 4049 | 32.6% |
| CM 19002 | 7% |
| EURACAMIDE | .2% |
| IR 1070 | .2% |

In both Examples 12 and 13, samples were produced on a commercial blown film line. The samples were tested at 300% extension in the traverse direction.

In Table VI, the results of the comparative hysteresis data are listed. As shown, the tensile set of Example 13 (Exxpol Plastomer) was 22% compared to the 38% for the sample of 12 (EVA) demonstrating a 72% improvement in the tensile set of the SBS/Exxpol plastomer film.

TABLE VI

Hysteresis Results @ 300% Extension (TD)

| SAMPLE ID | YAG MIL | MODULUS GRAMS | % TENSILE SET (%) |
|---|---|---|---|
| 012 | | | |
| Vector 7400D EVA | 2.664 | 545 | 38 |
| 013 | | | |
| Vector 7400D Exact 4049 | 2.651 | 323 | 22 |

The overall conclusions reached for these specific embodiments of the invention are that improvements to openability can be achieved by replacing the EVA with SSC EXXPOL plastomers. Also, substantial improvements to tensile set (elastic recoverability) can be achieved by replacing the KRATON SBC from Shell with the VECTOR 7400D SBC from Dexco. Ideally, the overall improvements afforded with the EXXPOL and Dexco VECTOR SBC used in combination not only improve tensile set, but processability as well. The improved openability afforded by these blends will not only reduce costs because of unnecessary additives (slip agents) but reduction in the amount of the SBC component as well. This particular embodiment will prove beneficial to convertors who use film produced from this invention in that reduced slip levels will equate to longer run time due to reduced slowdowns caused by slip buildup.

While particular embodiments of the present invention have been illustrated and described, it would be obvious to those skilled in the art that various changes and modifications can be made without departing from the spirit and scope of the invention. The appended claims are intended to cover all such modifications that are within the scope of this invention.

What is claimed is:

1. A method for producing an elastic film, comprising:

(a) providing i) from 20 to 70% by weight of a monoalkenyl arene-diene elastomeric block copolymer: and ii) an ethylene copolymer of ethylene and at least one comonomer said ethylene copolymer having a density in the range of about 0.86 to about 0.90 g/cm$^3$. a MWD in the range of about 2 to 6 an ethylene crystallinity less than 35%: and (b) converting said elastomeric block copolymer and said ethylene copolymer into a film by a film making process of slit-die extrusion, cast die extrusion, cast/embossed extrusion processing or blown film.

2. The method of claim 1 wherein the film conversion is a cast film process comprising:

(a) extruding the blend composition through a die having a gap greater than about 5 mils and less than 20 mils;

(b) expanding the extrudcd film to a thickness of between 0.5 mils and about 15 mils; and (c) rapidly cooling the expanded film.

3. The method of claim 1 wherein said film is oriented to a total draw down ratio in the range of about 2:1 to about 100:1 through a blown film or cast film die.

4. A process for producing an elastomeric film comprising: feeding a polymer blend to an extruder to provide an elastomeric film, said polymer blend including:

i) a first component selected from the group consisting of a styrene isoprene block copolymer and a styrene butadiene block copolymer, wherein said styrene is present in said block copolymer in the range of from 25 to 30% by weight of the block copolymers, wherein said first component is present in said blend in the range of from about 45 to about 65% by weight; and ii) a second component said second component being an ethylene α-olefin copolymer having a density from about 0.86 to 0.900 g/cm$^3$, said ethylene α-olefin copolymer having 1) a molecular weight distribution in the range of from 2 to 3.5;

2) a melt index from 1 to 10 dg/min.; and 3) a CDBI greater than 70%;

wherein said elastomeric film has a tensile set after one cycle of 150% extension in the machine or transverse direction of less than 20%.

* * * * *